(12) United States Patent
Rossi

(10) Patent No.: US 8,909,333 B2
(45) Date of Patent: Dec. 9, 2014

(54) DEVICE FOR MEASURING IMPEDANCE OF BIOLOGIC TISSUES

(75) Inventor: Stefano Rossi, Siena (IT)

(73) Assignee: STMicroelectronics S.R.L., Agrate Brianza (MB) (IT)

( * ) Notice: Subject to any disclaimer, the term of this patent is extended or adjusted under 35 U.S.C. 154(b) by 865 days.

(21) Appl. No.: 13/033,285

(22) Filed: Feb. 23, 2011

(65) Prior Publication Data
US 2011/0208028 A1 Aug. 25, 2011

(30) Foreign Application Priority Data
Feb. 24, 2010 (IT) .............................. VA2010A0017

(51) Int. Cl.
*A61B 5/00* (2006.01)

(52) U.S. Cl.
USPC ........................................................ 600/547

(58) Field of Classification Search
USPC ........................................................ 600/547
See application file for complete search history.

(56) References Cited

U.S. PATENT DOCUMENTS

| | | | |
|---|---|---|---|
| 3,652,930 A * | 3/1972 | Sugiyama et al. ............ | 324/615 |
| 4,909,261 A | 3/1990 | Rothenberg ................... | 128/734 |
| 6,995,607 B2 * | 2/2006 | Dosho et al. .................. | 327/558 |
| 7,319,851 B2 * | 1/2008 | Klumperink et al. ......... | 455/323 |
| 7,761,071 B2 * | 7/2010 | Miyasita et al. ........... | 455/232.1 |
| 7,796,060 B2 * | 9/2010 | Oberhuber et al. ............. | 341/94 |
| 2009/0234262 A1 | 9/2009 | Reid, Jr. et al. ............... | 601/152 |

OTHER PUBLICATIONS

Ross, Alexander, et al., "Current source design for electrical impedance tomography," Physiological Measurement 24 (2003) Institute of Physics Publishing Ltd., UK, pp. 509-516.

* cited by examiner

*Primary Examiner* — Max Hindenburg
(74) *Attorney, Agent, or Firm* — Allen, Dyer, Doppelt, Milbrath & Gilchrist, P.A.

(57) ABSTRACT

A device for measuring impedance of biological tissue may include a pair of electrodes for contacting the biological tissue, and a drive circuit coupled to the pair of electrodes and configured to drive an alternating current (AC) through the biological tissue and to sense an AC voltage. The AC voltage is towards a reference voltage on at least one of the pair of electrodes. The device may include at least one single-ended amplitude modulation (AM) demodulator configured to demodulate the AC voltage and to generate a corresponding baseband voltage representing the impedance, and an output circuit configured to generate output signals representative of DC and AC components of the baseband voltage.

17 Claims, 5 Drawing Sheets

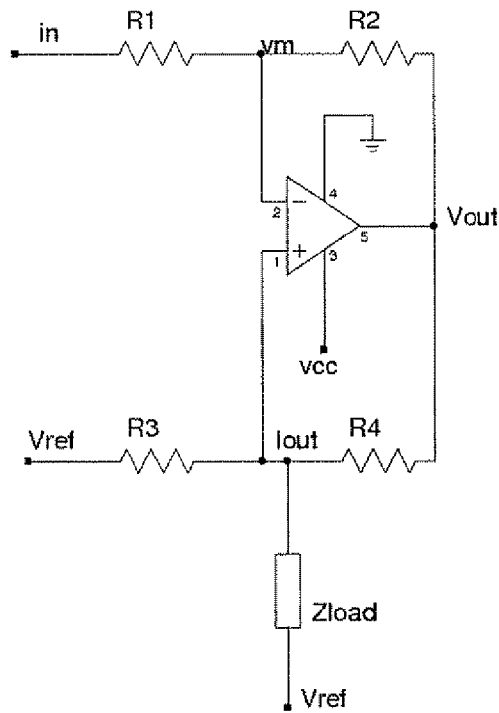
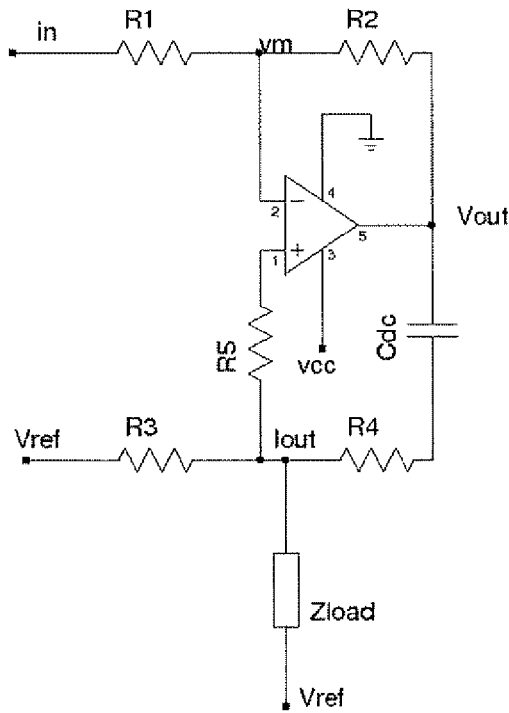
FIG. 5A  FIG. 5B
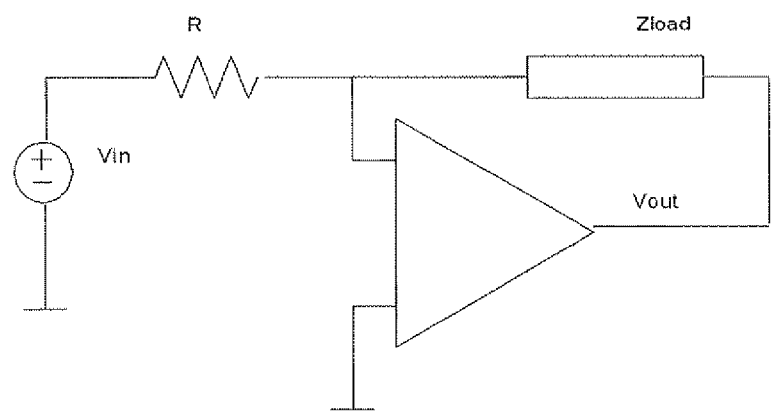
FIG. 6

DEVICE FOR MEASURING IMPEDANCE OF BIOLOGIC TISSUES

FIELD OF THE INVENTION

This invention relates to measurement instruments, and, more particularly, to a device for measuring impedance of biological tissues.

BACKGROUND OF THE INVENTION

Measurements of electrical impedance of the human body (bioimpedance) have been studied in bioengineering since the 1960s. These measurements include forcing an alternating current (AC) through the body (usually at a frequency higher than 10 kHz to avoid interference with the electrical activity of nervous and muscular tissues), and sensing the voltage drop between two points.

Water and generally all body fluids (blood, intra and extra cellular fluid, for example) provide the conductive medium of the body. Several measures and studies have been carried on applying this technique in different parts or regions of the body and using different frequencies to target different biological information (See, for example, Deok-Won Kim, Detection of physiological events by impedance, *Yonsei Medical Journal*, 30(1), 1989). In numerous applications the absolute value of the bioimpedance may be determined because it may be relatively simple to calculate it and it may provide much information. In other applications, both the modulus and phase of the complex bioimpedance may be measured.

It may be relatively difficult to determine relatively precise and reliable mathematical models of bioimpedance, particularly in thoracic regions. The main factors influencing electrical impedance in the chest may be the blood in the heart and in the aorta, and the pleural fluids and pulmonary circulation. Heart pumping, causing a variable distribution of blood in the heart-aorta region, and respiration, may be responsible for small variations of thoracic bioimpedance (i.e. the impedance of biological tissues). From these variations it may be possible to determine heart rate, breath rate, and evaluating cardiac output (volume of blood pumped by the heart for unity of time).

The measurements may be carried out using two or four electrodes, as schematically shown in FIG. 1. By using two electrodes, the measured impedance is the sum of the bioimpedance Zbody and of the contact impedance Ze at the electrodes. Generally, the impedance Ze disturbs the measure of the impedance Zbody. Using a four electrode setup, it may be possible to measure the impedance Zbody as the ratio between the measured voltage drop and the current forced through the body tissue with relatively more precision because the measurement may not be affected by the contact impedance Ze.

There may be a relatively strong interest in methods of carrying out this measure. Since it is a non-invasive technique, it may be correlated to a vast range of physiological parameters, thus, it may have a strong potential in many medical fields. Furthermore, the relative simplicity of the measurement, the integrability, the reduced size, and the low cost of the equipment, may make the technique of measuring thoracic bioimpedance particularly suitable to be implemented in wearable or implantable health monitoring systems.

The voltage $V_Z(t)$ sensed on the electrodes is an AC signal modulated by the bioimpedance $Z(t)$:

$$V_Z(t) = Z(t)I_0 \sin(\omega t)$$

With an AM demodulator it may be possible to obtain a baseband signal representing the modulus $|Z(t)|$ of the impedance. The phase of $Z(t)$ may be evaluated, for example, by measuring the delay between the input current and output voltage or with a phase and quadrature demodulation.

A block diagram of a typical circuit for measuring the impedance of a biological tissue is illustrated in FIG. 2. An AC voltage generated by an oscillator is used to control a voltage-to-current converter that delivers a current Iz that is injected through the biological tissue using two or four electrodes. The voltage on the biological tissue is sensed, amplified, and AM demodulated for obtaining a baseband signal. The DC component Z0 and the AC component deltaZ of the baseband signal are extracted using a low-pass filter LPF and a high-pass filter HPF and converted into digital form by an analog-to-digital converter ADC.

A sinusoidal voltage may not be used, but it may be desirable to reduce the attenuation of higher harmonics due to capacitive effects and to use an envelope detector as an AM demodulator. Furthermore the use of an adjustable sinusoidal waveform may make frequency analysis and characterization of tissues possible.

This type of system may be characterized by the presence of an instrumentation amplifier (INA) upstream from the AM demodulator. A drawback of this signal processing path is that the INA works on the modulated input signal. For this reason, the known architecture of FIG. 2 generally requires either an INA of a sufficiently large bandwidth, and, thus, has a large current consumption, or use of a low frequency for the injected current. This is a limitation because INAs, especially low power consumption and low cost devices, usually have a relatively narrow bandwidth.

Another point of the architecture of FIG. 2 is the voltage-to-current converter. It may be desirable that this circuit have a relatively large output impedance to provide negligible variations of the amplitude of the injected current when the load varies, and be DC decoupled for safety reasons, because it is desirable that DC current forced through human body tissue be less than 10 µA under normal conditions and less than 50 µA in single fault condition (See, Association for the Advanced of Medical Instrumentation. Medical electrical equipment—Part 1: General requirements for basic safety and essential performance. *ANSI/AAMI ES60601-1:2005*).

As disclosed in Rafael Gonzalez-Landaeta, Oscar Casas, and Ramon Pallas-Areny, Heart rate detection from plantar bioimpedance measurements, *IEEE Transactions on Biomedical Engineering*, 55(3):1163-1167, 2008, another known measurement system is depicted in FIG. 3. AM demodulation is performed upstream from the INA to increase the Common Mode Rejection Ratio (CMRR). The circuitry is fully differential, and a differential stage with coupled amplifiers is used as the first stage of the voltage drop on the electrodes. A high pass filter HPF and amplifier stage are used for extracting the AC components of the signal, deltaZ, that, in many applications (for example, thoracic bioimpedance measurement) includes physiological information.

The bandwidth of such a system is limited by the coupled amplifiers stage. The higher the gain (that is, greater than one), the lower the bandwidth. The working frequency used in Rafael Gonzalez-Landaeta, Oscar Casas, and Ramon Pallas-Areny, Heart rate detection from plantar bioimpedance measurements, *IEEE Transactions on Biomedical Engineering*, 55(3):1163-1167, 2008, for example, is fixed at 10 kHz, which is relatively small.

SUMMARY OF THE INVENTION

A relatively high precision device and a relative method for measuring the impedance of biological tissues using two or four electrodes has now been found. The device does not use any differential amplifier of the sensed voltage on the electrodes because it comprises a single-ended AM demodulator of the voltage towards ground on at least one sensing electrode, and an output circuit configured to generate an output signal representative of the impedance corresponding to the DC component of the baseband voltage.

According to an embodiment, the device comprises a circuit configured to force an AC current throughout the biological tissue through two electrodes. The device also includes two single-ended AM demodulators, respectively, configured to demodulate the voltages towards ground of two electrodes. The output circuit includes a differential amplifier configured to amplify the baseband demodulated single-ended voltages, and a filter for extracting the DC and the AC components of the differential baseband voltage.

According to yet another embodiment, the device comprises two single-ended AC buffers of the voltages towards ground on the electrodes. Each one of the two AM demodulators demodulate the voltage stored in a respective buffer. According to yet another embodiment, the circuit configured to force a current throughout the biological tissue is a voltage-to-current converter including an operational amplifier coupled to the electrodes and is configured to generate, on an output node, a signal representative of the voltage drop on the biological tissues.

According to yet another embodiment, the voltage-to-current converter is a Howland voltage-to-current converter controlled by an AC voltage generator. The voltage drop towards ground on an electrode may be provided on an output node of the Howland converter.

According to yet another embodiment, the voltage-to-current converter may include a DC-blocking capacitor of a DC current injected throughout the biological tissue, and a fault protection resistor configured to limit the current injected through body tissues in case of faults of the voltage-to-current converter. According to yet another embodiment, the circuit configured to force an AC current may be coupled to the electrodes through capacitors.

This disclosure also provides a Howland voltage-to-current converter configured to force a current, determined by an input voltage, through a load connected between two output terminals of the converter. The Howland voltage-to-current converter may include a first resistive voltage divider defined between a reference node and an input node configured to receive the input voltage. The Howland voltage-to-current converter may also include a second resistive voltage divider having the same voltage ratio of the first resistive voltage divider, and connected between a first output terminal of the converter and the common reference node through a DC filter capacitor. The middle terminal of the second resistive voltage divider may be a second output terminal of the converter.

The Howland voltage-to-current converter may also include an operational amplifier, an output of which is the common reference node, an input of which is connected to the middle node of the first resistive voltage divider, and the other input of which is coupled to the middle node of the second resistive voltage through a current limiting resistor.

BRIEF DESCRIPTION OF THE DRAWINGS

FIG. 5a schematically illustrates a Howland voltage-to-current converter.

FIG. 5b schematically illustrates a Howland voltage-to-current converter having a DC-blocking capacitor and a fault protection resistor.

FIG. 6 schematically illustrates an exemplary voltage-to-current converter alternative to the Howland converter.

DETAILED DESCRIPTION OF THE PREFERRED EMBODIMENTS

Figure 3:
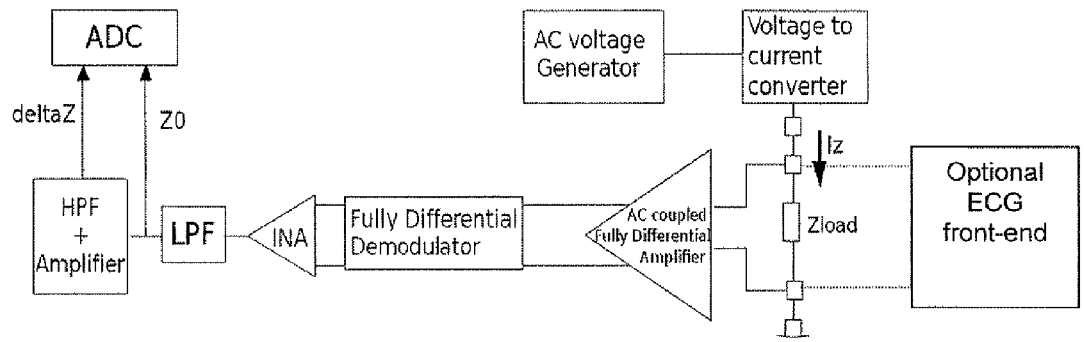
FIG. 3 schematically illustrates yet another architecture for measuring impedance of biological tissues in accordance with the prior art.
Figure 4:
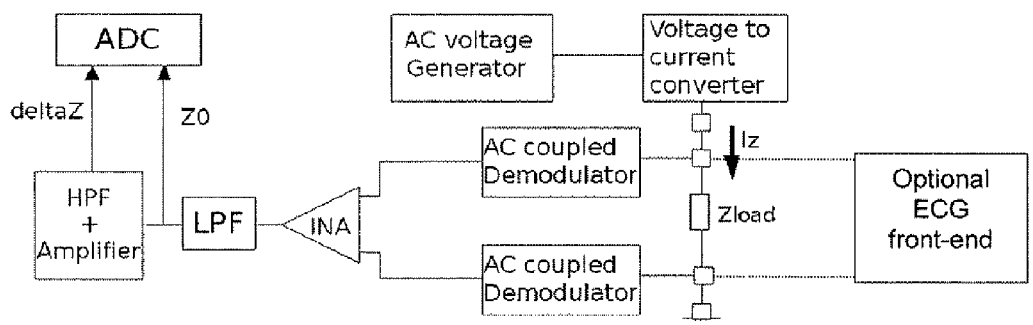
FIG. 4 schematically illustrates an embodiment of a device for measuring impedance of biological tissues in accordance with the present invention.

An embodiment of a device for measuring the impedance of biological tissue is illustrated in FIG. 4. The circuit blocks in common with the prior devices of FIGS. 2 and 3 are identified by the same labels.

The device has two single-end AM demodulators. Each demodulates the voltage towards ground of a respective electrode and generates a respective baseband signal. The demodulated baseband signals are supplied in input to an INA that generates an amplified copy of their difference.

Figure 1:
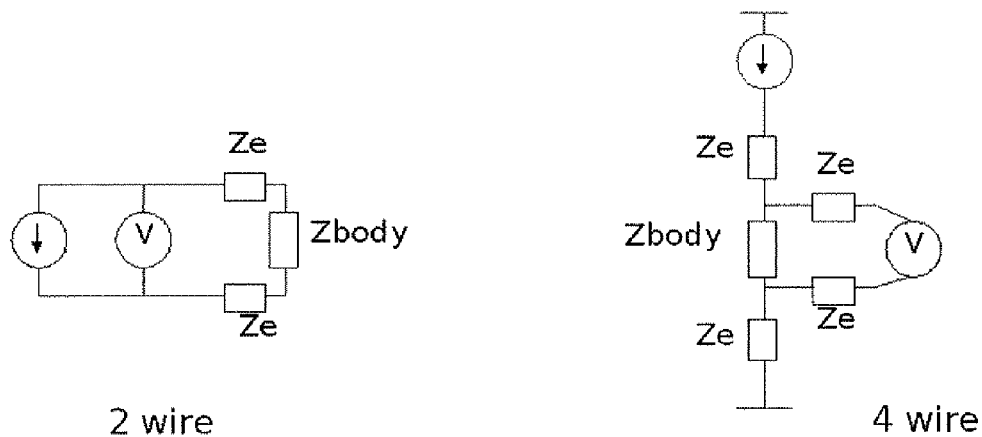
FIG. 1 schematically illustrates two architectures for measuring the impedance of a biological tissue in accordance with the prior art.
Figure 2:
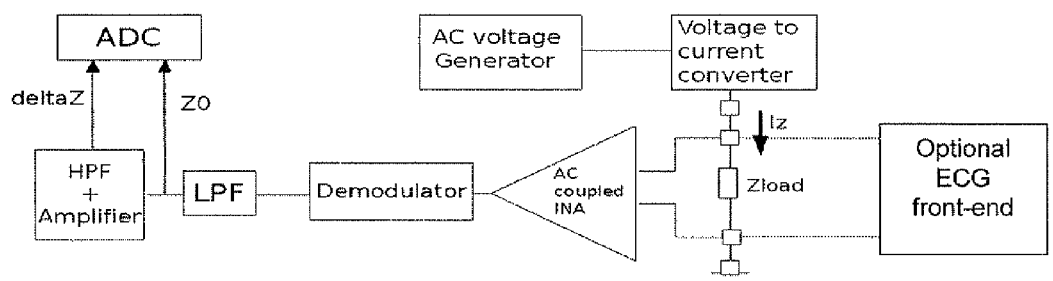
FIG. 2 schematically illustrates another architecture for measuring the impedance of a biological tissue in accordance with the prior art.

Differently from the known device of FIG. 2, the INA amplifies a baseband signal, thus, it has a relatively large gain and a good CMRR in the baseband range of frequencies. Therefore it may be possible to use a low cost and low power consumption INA.

Differently from the prior device of FIG. 3 disclosed in Rafael Gonzalez-Landaeta, Oscar Casas, and Ramon Pallas-Areny, Heart rate detection from plantar bioimpedance measurements, *IEEE Transactions on Biomedical Engineering*, 55)3):1163-1167, 2008, the device may not need a differential amplifier of the voltage drop sensed on the electrodes because, in the device, the AM demodulation is carried out in a single-end fashion. In a coupled amplifiers architecture, the bandwidth is reduced the more the gain is greater than one.

Preferably, the voltages towards ground of the two electrodes are read by two single ended AC coupled buffers, thus rejecting electrode offset rejection and high input impedance before being AM demodulated. This approach is preferred because unitary gain buffers have the largest bandwidth for a given operational amplifier, and, at the same time, the very good match of the unitary gain provides a good CMRR. Noise, that is a reason for which a gain in the first stages is usually preferred, is generally not an issue in this case because the first stage works on a relatively high frequency signal in a bandwidth in which the noise of common operational amplifiers is relatively low.

Any skilled person will be capable of identifying AC buffer architectures configured to be used in the device, and for this reason, they are not illustrated in detail. In a four electrode configuration, as the architecture shown in FIG. 4, an ECG front-end may optionally be coupled to measure also the electrocardiogram of a patient.

The voltage-to-current converter may be a Howland voltage-to-current converter or, more generally, any voltage-to-current converter. An exemplary voltage-to-current converter may be the converter illustrated in FIG. 6. The functioning of this exemplary converter is relatively straightforward and will not be explained in detail.

Another voltage-to-current converter is the classic Howland converter illustrated in FIG. 5a. This architecture may be considered unsafe for applications on the human body because it generally does not protect the body against overcurrents due to eventual fault conditions and DC currents eventually injected throughout the body.

The load current is $$I_Z = \frac{-\frac{R_2}{R_1}(V_{in} - V_{ref})}{R_4 + \left(\frac{R_4}{R_3} - \frac{R_2}{R_1}\right) Z_{load}}$$

in which Vin is the driving voltage. If $$\frac{R_4}{R_3} = \frac{R_2}{R_1} \qquad (1)$$

the current Iz is independent on the load impedance Zload. If the driving voltage Vin of the Howland circuit is an AC signal centered around the reference voltage Vref, then no DC current flows through the load. Unfortunately, this condition may not be guaranteed, for example, in the case of a single fault on the operational amplifier (i.e. one of the pins of the amplifier shorted to ground or to the supply).

A Howland converter with protections against overcurrents and DC currents, thus configured to be used for applications on the human body, is illustrated in FIG. 5b. The capacitor blocks a DC current flowing through the load from the output of the operational amplifier, in case of a fault on the output of the amplifier or of the generator. This capacitor may not impact the normal functionality if the working frequency is much greater than 1(Cdc·R4). The resistor R5 works as a current limiter in case of a fault on the positive input of the operational amplifier.

Figure 7:
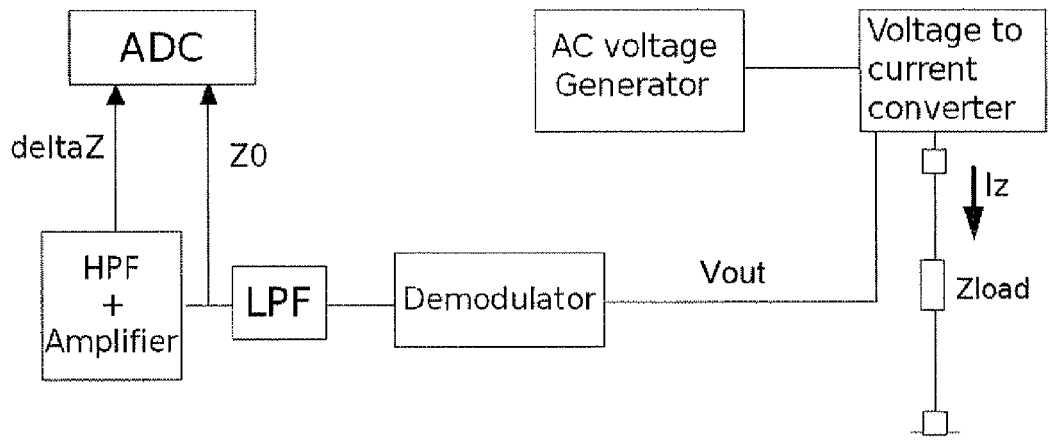
FIG. 7 schematically illustrates yet another embodiment of a device for measuring impedance of biological tissues that does not include an INA in accordance with the present invention.

The architecture of FIG. 4 may be further simplified by using the Howland voltage-to-current converter or the voltage-to-current converter of FIG. 6, or more generally, any voltage-to-current converter including an operational amplifier coupled to the electrodes and configured to generate, on an output node, a signal representative of the voltage drop on the biological tissue, in the scheme of FIG. 7. In these configurations the INA may no longer be desired because the Howland voltage-to-current converter has a relatively small output impedance. The output voltage Vout and the single-end baseband demodulated signal have an amplitude sufficient for being processed.

Even if the architecture of FIG. 7 is less precise in measuring the impedance Zload because it uses only two electrodes, it is relatively less complex, has a relatively smaller size, reduced power consumption, and reduced costs. In some applications a refined precision may not be required, for example, for sensing the breathing rate from thoracic impedance, and thus, the above architectures may conveniently be used.

The device of FIG. 7, or of FIG. 4, may not be suitable for being connected with a two lead EGG front-end as in the prior device of FIG. 3 if only two electrodes are used. This may be a limitation because, in many applications, as for measures on the human thorax, for example, the simultaneous bioimpedance and ECG recording may be useful or even desired.

Figure 8:
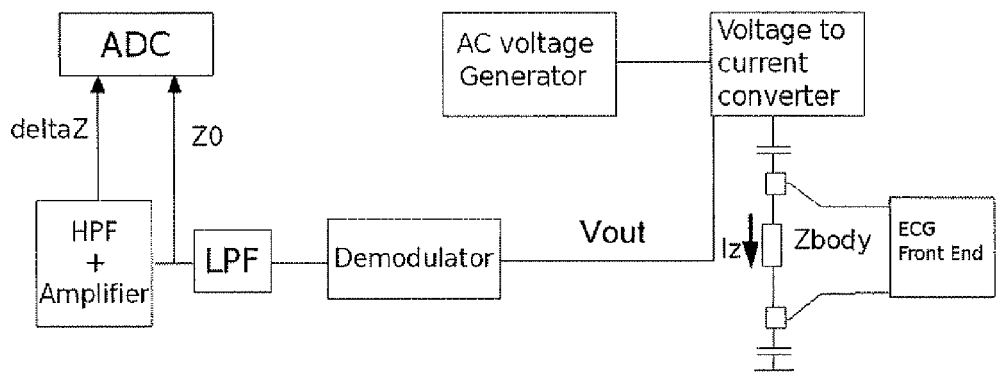
FIG. 8 schematically illustrates yet another embodiment of a device for measuring impedance of biological tissues having DC-blocking capacitors and being connected to an ECG device in accordance with the present invention.

This eventual limitation may be overcome in the device of FIG. 8. Two capacitors have been added to decouple, at low frequencies, the electrodes from the voltage-to-current converter. The impedance of capacitors sums up to the impedance of electrodes and to the bioimpedance, and may alter measurements. For this reason, it is desirable that the value of the capacitors be large enough to give an acceptably small impedance at the working frequency. On the other hand, it is desirable that the capacitors not be too large, otherwise this may cause an attenuation of the EGG.

Moreover, the frequency of the pole associated with the capacitors depends on unknown parameters, such as, for example, electrode to skin contact impedance and body impedance. For this reason, the choice of the value of capacitors may be of a particular importance.

Appropriate values of these capacitors may range from 1 nF to 100 nF, if the thoracic impedance is to be measured. Different values may be chosen depending on the particular application for which the device is designed.

Figure 9:
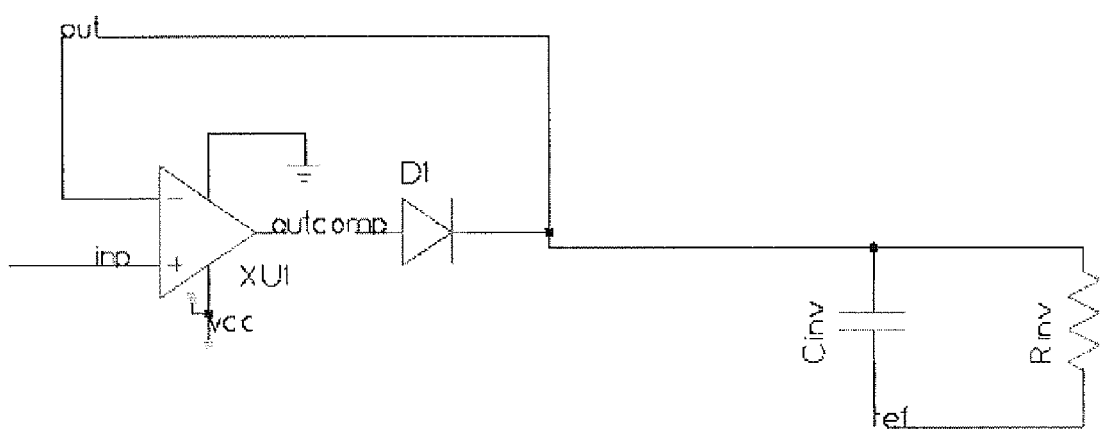
FIG. 9 schematically illustrates an AM demodulator configured to be used in the device for measuring impedance of biological tissues in accordance with the present invention.

The AM demodulator used in the device may be of any kind. According to a preferred embodiment, the AM demodulator is as illustrated in FIG. 9. It includes an envelope demodulator D1-Cinv-Rinv and a comparator XU1 that generates a logic comparison signal OUTCOMP as the result of the comparison between the input signal INP to be AM demodulated and the output signal OUT.

Differently from commonly used AM demodulators, the demodulator of FIG. 9 has a feedback comparator instead of an operational amplifier. This causes the output of the comparator to oscillate as long as the input signal attains its peak value. Then the diode becomes reversely biased, and the output of the comparator switches low. This may not significantly alter the demodulated voltage because the output low-pass filter cut-off frequency is much lower than the bandwidth of these spikes. When the input voltage INP increases, the output of the comparator almost immediately switches high.

By contrast, if an operational amplifier were used instead of the comparator XU1, the output recovery time after saturation and the slew-rate of the amplifier would limit the speed with which the signal OUTCOMP switches high. As a consequence, it may not be possible to demodulate AM signals at relatively high frequencies unless a relatively expensive and power consuming high frequency operational amplifier is used.

The AM demodulator of FIG. 9 thus may be conveniently employed in many applications where demodulation of high frequency AM signals is desired. The devices may be integrated in small packages and may operate in a range of frequencies up to 100 kHz with a relatively small power consumption (about 2.5 mW). However, this is just an example, since higher working frequencies may be obtained using faster components in the voltage to current converter and demodulator stages.

These characteristics make the devices suitable for a vast range of bioimpedance measures and applications. The flexibility and reduced dimensions may make it ideal for wearable applications, both in a clinical environment or in home monitoring tasks, such as, a band-aid, a T-shirt, or a bangle. Examples of measurements that may be carried out with the devices are the monitoring of breath rate, heart rate, and other heart related parameters in thoracic bioimpedance, body composition analysis, or local impedance measures in limbs. When relatively high precision measures are desired, the four electrode architecture may be preferred.

That which is claimed:

1. A device for measuring impedance of biological tissue comprising:
   a pair of electrodes for contacting the biological tissue;
   a drive circuit coupled to the pair of electrodes and configured to drive an alternating current (AC) through the biological tissue and to sense an AC voltage;
   at least one single-ended amplitude modulation (AM) demodulator configured to demodulate the AC voltage and to generate a corresponding baseband voltage representing a modulus of the impedance; and
   an output circuit configured to generate output signals representative of DC and AC components of the baseband voltage.

2. The device of claim 1, further comprising a second pair of electrodes; and wherein said at least one single-ended AM demodulator comprises a first single-ended AM demodulator configured to demodulate the AC voltage on one of said second pair of electrodes, a second single-ended AM demodulator configured to demodulate the AC voltage on another of said second pair of electrodes, and a differential amplifier having an input configured to receive the demodulated AC voltages generated by the first and second AM demodulators and configured to generate the baseband voltage.

3. The device of claim 2,
   further comprising an AC voltage buffer coupled between one of said second pair of electrodes and one of said first and second single-ended AM demodulators, respectively, wherein said AC voltage buffer is configured to store the AC voltage of the one of said second pair of electrodes.

4. The device of claim 2, wherein said drive circuit comprises a voltage-to-current converter including an output node and amplifier coupled to said first pair of electrodes and configured to generate, on the output node, a signal representative of a voltage drop on the biological tissue.

5. The device of claim 4, wherein said voltage-to-current converter comprises a Howland voltage-to-current converter comprising:
   an input node configured to receive an AC drive voltage;
   a first resistive voltage divider having a middle terminal and coupled between the output node and the input node;
   a direct current (DC) filter capacitor;
   a second resistive voltage divider having a middle terminal and the same voltage ratio as said first resistive voltage divider and coupled between a common terminal with one electrode of one of said first and second pairs of electrodes and the output node through the DC filter capacitor, another electrode of the one of said first and second pairs of electrodes coupled to the middle terminal; and
   a current limiting resistor;
   said amplifier having a first input coupled to the middle terminal of said first resistive voltage divider and a second input coupled to the middle terminal of the second resistive voltage through the current limiting resistor.

6. The device of claim 1, wherein said drive circuit comprises a voltage-to-current converter including an output node and an amplifier coupled to said pair of electrodes and configured to generate, on the output node, a signal representative of a voltage drop on the biological tissue.

7. The device of claim 6, wherein said voltage-to-current converter comprises a Howland voltage-to-current converter coupled to said at least one single-ended AM demodulator such that said at least one single-ended AM demodulator is configured to demodulate the AC voltage on the output node, and wherein the Howland voltage-to-current converter comprises:
   an input node configured to receive an AC drive voltage;
   a first resistive voltage divider having a middle terminal and coupled between the output node and the input node;
   a DC filter capacitor;
   a second resistive voltage divider having a middle terminal the same voltage ratio as said first resistive voltage divider and coupled between a common terminal with one of said pair of electrodes and to the output node, another one of said pair of electrodes being coupled to the middle terminal; and
   a current limiting resistor;
   said amplifier having a first input connected to the middle node of said first resistive voltage divider and a second input coupled to the middle terminal of the second resistive voltage divider through said current limiting resistor.

8. The device of claim 6, further comprising a plurality of DC blocking capacitors coupling said voltage-to-current converter to said pair of electrodes.

9. The device of claim 8, wherein each of said plurality of DC-blocking capacitors has a same value.

10. The device of claim 8, wherein the value of each of said plurality of DC-blocking capacitors has a capacitance value in a range from 1 nF to 100 nF.

11. The device of claim 1, wherein said at least one single-ended AM demodulator comprises:
    a logic comparator configured to receive an AM modulated signal to be converted and the baseband voltage, said logic comparator also being configured to generate a logic comparison signal; and
    an envelope demodulator configured to receive the logic comparison signal and generate the baseband voltage.

12. A device for measuring impedance of biological tissue comprising:
    a pair of electrodes for contacting the biological tissue;
    a drive circuit coupled to the pair of electrodes and configured to drive an alternating current (AC) through the biological tissue and to sense an AC voltage; and
    at least one single-ended amplitude modulation (AM) demodulator configured to demodulate the AC voltage and to generate a corresponding output voltage representing a modulus of the impedance.

13. The device of claim 12, wherein said drive circuit comprises a voltage-to-current converter including an output node and an amplifier coupled to said pair of electrodes and configured to generate, on the output node, a signal representative of a voltage drop on the biological tissue.

14. The device of claim 13, wherein said voltage-to-current converter comprises a Howland voltage-to-current converter coupled to said at least one single-ended AM demodulator such that said at least one single-ended AM demodulator is configured to demodulate the AC voltage on the output node, and wherein the Howland voltage-to-current converter comprises:
    an input node configured to receive an AC drive voltage;
    a first resistive voltage divider having a middle terminal and coupled between the output node and the input node;
    a DC filter capacitor;
    a second resistive voltage divider having a middle terminal the same voltage ratio as said first resistive voltage divider and coupled between a common terminal with one of said pair of electrodes and to the output node, another one of said pair of electrodes being coupled to the middle terminal; and a current limiting resistor;

said amplifier having a first input connected to the middle node of said first resistive voltage divider and a second input coupled to the middle terminal of the second resistive voltage divider through said current limiting resistor.

15. The device of claim 13, further comprising a plurality of DC-blocking capacitors coupling said voltage-to-current converter to said pair of electrodes.

16. A method of measuring impedance of biological tissue comprising:

sensing an AC voltage through the biological tissue via two electrodes to be placed in contact with the biological tissue;

using at least one single-ended AM demodulator to demodulate the AC voltage and to generate a baseband voltage representing a modulus of the impedance; and generating output signals representative of DC and AC components of the baseband voltage.

17. The method of claim 16, further comprising driving an AC current through the biological tissue using a voltage-to-current converter including an amplifier coupled to the pair of electrodes to generate a signal representative of a voltage drop on the biological tissue.

* * * * *